United States Patent [19]
Ikematsu et al.

[11] Patent Number: 5,503,744
[45] Date of Patent: Apr. 2, 1996

[54] BIOLOGICAL OSCILLATING DEVICE

[75] Inventors: Mineo Ikematsu, Tsuchiura; Yukihiro Sugiyama; Masahiro Iseki, both of Tsukuba, all of Japan

[73] Assignee: Sanyo Electric Co., Ltd., Osaka, Japan

[21] Appl. No.: 317,397

[22] Filed: Oct. 4, 1994

[30] Foreign Application Priority Data

Oct. 7, 1993 [JP] Japan .................... 5-251337

[51] Int. Cl.⁶ .................... B01D 63/00; G01N 27/26
[52] U.S. Cl. .................... 210/257.2; 210/638; 204/403; 204/418; 422/82.01; 436/806
[58] Field of Search .................... 210/321.6, 257.2, 210/500.27, 638; 607/71, 76; 204/403, 418; 422/82.01; 436/151, 806, 179

[56] References Cited

U.S. PATENT DOCUMENTS

| | | | |
|---|---|---|---|
| 4,822,470 | 4/1989 | Chang | 435/173 |
| 4,970,154 | 11/1990 | Chang | 435/173 |
| 5,141,604 | 8/1992 | Ayers | 204/78 |
| 5,308,486 | 4/1994 | Chang | 435/287 |
| 5,358,931 | 10/1994 | Rubinsky et al. | 514/12 |
| 5,378,342 | 1/1995 | Ikematsu et al. | 204/403 |

FOREIGN PATENT DOCUMENTS 274889  10/1993  Japan .

OTHER PUBLICATIONS

Kiyoshi Toko, et al., "Phase Transition and Electric Oscillations in Synthesized Lipid Membranes", Department of Electronics, Faculty of Engineering, Review Article, Membranes, vol. 12, No. 1, 1987.

Kenichi Yoshikawa, "Artificial Neuron Membrane", Surface, vol. 26, No. 11 (1988).

*Primary Examiner*—Ana M. Fortuna
*Attorney, Agent, or Firm*—Loeb and Loeb

[57] ABSTRACT

A biological oscillating device comprises a lipid-impregnated membrane which is disposed in an electrolyte solution and in which is buried an ion channel having a selectivity opposite to that of the lipid-impregnated membrane, and an electrode provided for transmitting a membrane potential of the lipid-impregnated membrane in the form of an electrical signal. When a membrane potential is caused across the lipid-impregnated membrane by the application of an electric current via an eletrode, or by the activation of the ion pump, an ion pump, an ion channel opens once the magnitude of the membrane potential reaches the active potential of the ion channel, whereby the membrane potential is accordingly eliminated. Upon the elimination of the membrane potential, the ion channel is closed to allow the membrane potential to be again raised. Then, once reaching the active potential of the ion channel, the ion channel reopens so that the membrane potential is correspondingly eliminated. Through the repetition of such procedures, an oscillating electrical signal can be generated.

4 Claims, 4 Drawing Sheets

BIOLOGICAL OSCILLATING DEVICE

BACKGROUND OF THE INVENTION

1. Field of the Invention

The present invention relates to a biological oscillating device for generating a non-linear oscillating signal which is to be a factor of an electrical oscillation required for the transmission of information pertaining to the life maintenance of an organism, and more particularly to a biological oscillating device serving as a biomembrane model including as its fundamental structure a membrane such as a lipid membrane within which is arranged protein or polypeptide allowing various ions to be transported or passed, the device generating an oscillating electrical signal varying in response to an external stimulus such as light irradiation or chemical substance.

2. Description of the Related Arts

In information processing in a living body, an ignition of a nerve system and a movement of a substance between the inside and the outside of the cell are the source of information transmission. An electrical oscillation caused by such movement them is thought to be an oscillation produced by functions of proteins in an organism membrane. This oscillating signal varies diversely, depending on an external stimulus, whereby the stimulus information is transmitted to a central nerve.

As means for obtaining this oscillation artificially using an organic material, there is currently known a modeling device for obtaining an oscillating signal from a lipid membrane in an aqueous electrolyte solution. This is an electrical oscillation to be produced by a fluctuation of a lipid molecule. This prior art is exemplified by "Hyomen (Surface)" by Yoshikawa, Vol. 26, No. 11, 1988 and "Maku (Membrane)" by Toko and Yamafuji, Vol. 12, No. 1, 1987.

In the case where the above modeling device is used to constitute a biological oscillation device, however, it was inconveniently difficult to generate an oscillation having a specific mode in response to an external input, in other words, to control the oscillation.

SUMMARY OF THE INVENTION

The present invention was conceived in view of the above problems. It is therefore the object of the present invention to provide a biological oscillating device capable of generating an oscillating electrical signal in response to an external stimulus, and for it to be easily controllable.

In order to overcome the above problems, there is provided a biological oscillating device comprising an electrolyte solution stored in a container; a partition membrane for partitioning the electrolyte solution, the partition membrane including an ion channel buried thereinto, the ion channel having a cation selectivity and capable of opening when a potential difference between opposite sides of the partition membrane reaches a predetermined threshold value, the partition membrane having a selectivity reverse or considered to be reverse to the selectivity of the ion channel; means for causing a membrane potential within the partition membrane; an electrode for transmitting in the form of an electrical signal a variation in the membrane potential caused within the partition membrane; and the difference in concentration of the partitioned electrolyte solution being set in accordance with the selectivity of the partition membrane and of the ion channel.

In the above biological oscillating device, the means for causing a membrane potential within the partition membrane preferably includes an ion pump buried into the partition membrane, and means for conferring a stimulus onto the ion pump to activate the ion pump.

Referring to FIG. 1, description will be given of an action and a function of the biological oscillating device of the present invention having the above configuration.

Even though a membrane potential is caused by the means for causing a membrane potential within the partition membrane, the membrane potential will present no variation until its magnitude reaches the active potential of the ion channel (See (a) in FIG. 1). This arises from the fact that the overall selectivity of the membrane is invariable until the magnitude of the membrane potential reaches the active potential.

However, once the magnitude of the membrane potential caused within the partition membrane reaches the active potential of the ion channel, the membrane potential repeatedly fluctuates to generate a predetermined oscillating signal. The reason is as follows.

That is, when the magnitude of the membrane potential reaches the active potential of the ion channel, the ion channel opens. Upon the instant, the overall selectivity of the membrane is governed by the selectivity of the ion channel. This will instantaneously induce a reversal of the selectivity of the membrane, whereupon the resistance of the membrane drops in proportion to the amount of conductance increased by the ion channel. When the membrane resistance drops, the membrane potential is instantaneously reduced with the result that the ion channel is closed. This will allow the overall selectivity of the membrane to return to its original selectivity, so that the membrane resistance is again raised along with another increment of the membrane potential. Then, when the membrane potential is again increased to reach the active potential of the ion channel, the ion channel reopens to allow the membrane potential to drop at that instant.

Thus, by conferring a potential sufficient to open the ion channel across the partition membrane, certain procedures are repeated, including, in the mentioned order, the opening of the ion channel, the reduction in the membrane potential caused by the reversal of the selectivity, the closure of the ion channel, the increase in the membrane potential difference, the opening of the ion channel, and the reduction in the membrane potential caused by the reversal of the selectivity; whereby a predetermined fluctuating phenomenon can be obtained. This fluctuating phenomenon is derived from the electrode in the form of an oscillating electrical signal (See (b) in FIG. 1).

In the case where an ion pump is buried in the partition membrane of the biological oscillating device, the ion pump is activated to transport ions to cause a membrane potential across the membrane, so that the ion channel is opened or closed in accordance with the magnitude of this membrane potential. Thus, this ion pump serves as means for conferring a membrane potential for opening the ion channel across the partition membrane.

Besides, in a case where the magnitude of the membrane potential significantly surpasses the active potential, there may appear a disturbance in the waveform of the oscillating signal. This is supposed to arise from the fact that the excessive membrane potential will accelerate the interaction among ion channels, and complicate their opening and closing actions.

DESCRIPTION OF THE PREFERRED EMBODIMENTS

Preferred exemplary embodiments of the present invention will now be described with reference to the accompanying drawings.

[Configuration of Device]

Figure 1:
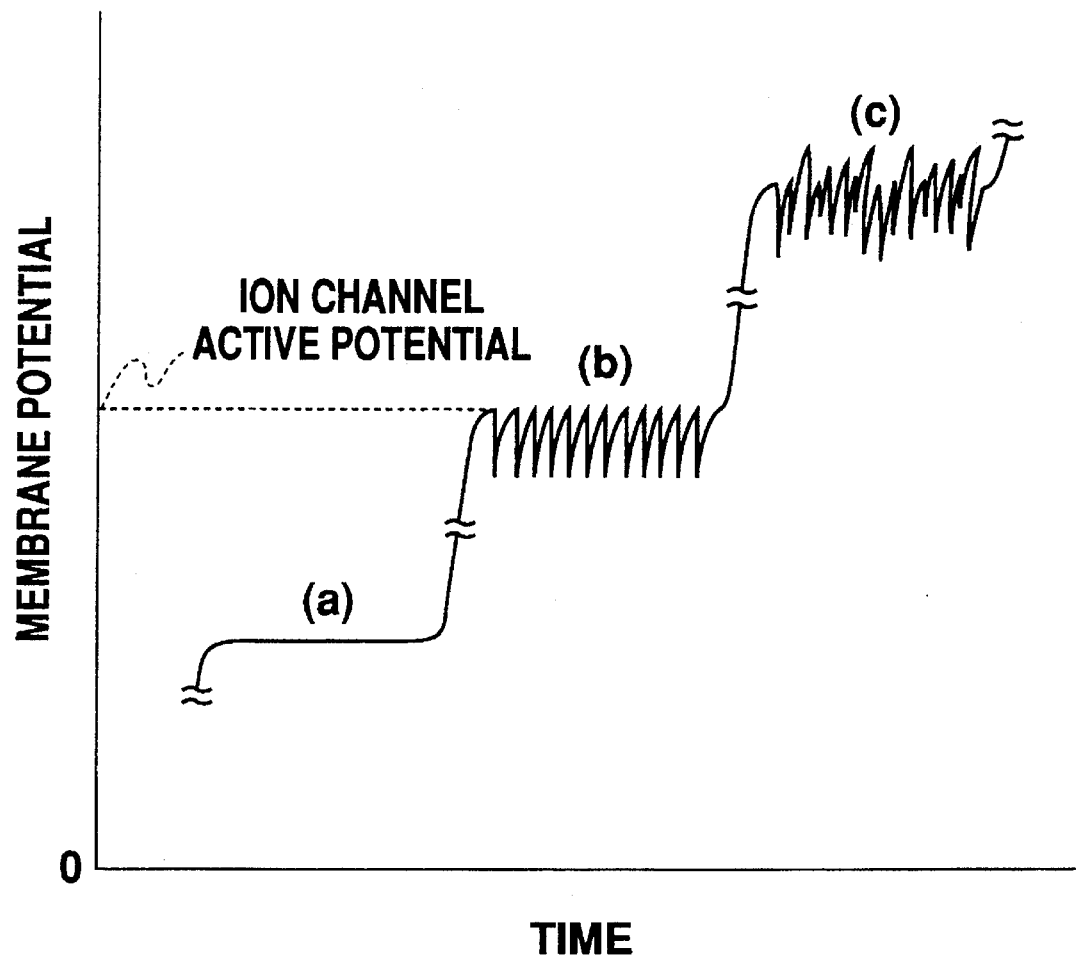
FIG. 1 is a diagram for explaining the operation of a biological oscillating device configured in accordance with the present invention.
Figure 2:
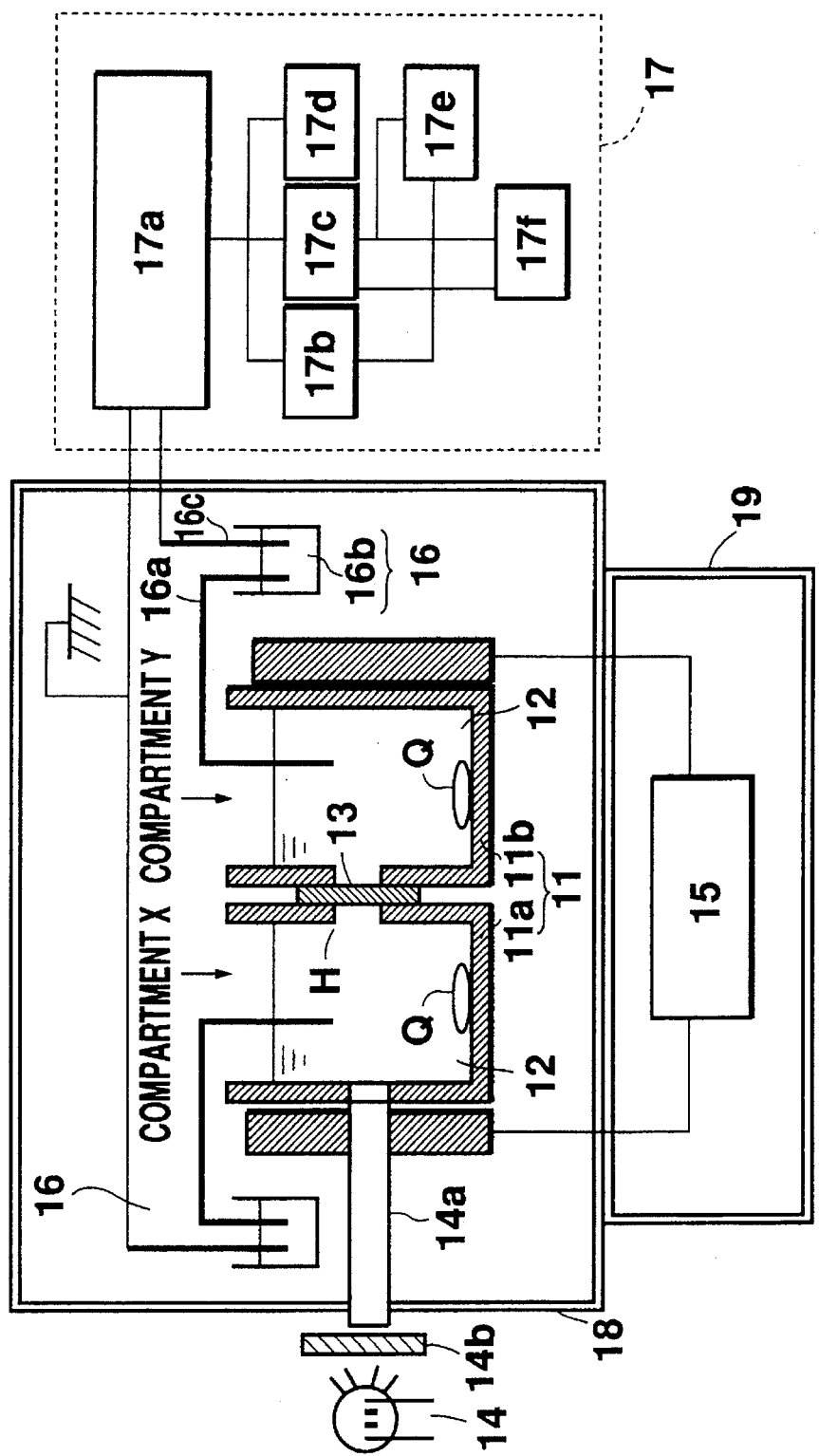
FIG. 2 schematically illustrates a membrane potential measuring system of the biological oscillating device according to a preferred embodiment of the present invention.

FIG. 2 is a block diagram depicting a configuration of a biological oscillating device according to a preferred embodiment of the present invention.

The biological oscillating device of this embodiment comprises a cell 11 including cells 11a and 11b integral with each other, the cells 11a and 11b defining compartments X and Y, respectively. The cell 11 has a hole H fitted with, in this embodiment, a lipid-impregnated membrane 13 serving as a partition. The compartments X and Y are filled with an electrolyte solution 12 and partitioned by the lipid-impregnated membrane 13. The temperature of the electrolyte solution 12 being stored within each of compartments X and Y is equalized by stirring with a stirrer bar Q.

The biological oscillating device of this embodiment further comprises a light source 14 and a light guide 14a to irradiate the lipid-impregnated membrane 13 with light. Rays of light emitted from the light source 14 are directed to the interior of the cell through the light guide 14a.

The cell 11 is preferably made of a material resistant to organic solvent, in view of the properties of the lipid-impregnated membrane 13, such as a fluorocarbon polymer in this embodiment. The temperature of the electrolyte solution 12 within the cell 11 is controlled by a circulator 15. The compartments X and Y are each provided with an electrode 16 consisting of a salt bridge 16a, 1 mol/l of KCl aqueous solution 16b, and a silver/silver chloride electrode 16c. Thus, in this embodiment, the electrodes are placed in the respective cells defined by partitioning the fluorocarbon polymer cell by the lipid-impregnated membrane 13. The compartment X is connected to ground in this embodiment.

Oscillating electrical signals derived from the electrodes 16 are sent to an information processing unit 17 composed of a patch-clamp amplifier 17a, an oscilloscope 17b, a filter 17c, a tape recorder 17d, a chart recorder 17e, and a computer 17f. The patch-clamp amplifier 17a serves to cause a potential difference across the lipid-impregnated membrane 13 by way of the electrodes 16.

It is to be noted in the above lipid-impregnated membrane measuring system that a shield box 18 and an antivibrator 19 are provided to take measures against noise including sound-proof and vibration-proof effects. Also, the light source 14 is disposed outside the shield box 18, and a heat absorption filter 14b is placed between the light guide and the light source so as not to allow thermal conduction to the lipid-impregnated membrane measuring system.

[Method of Preparing Lipid-impregnated Membrane]

A lipid-impregnated membrane is a membrane being impregnated with lipid, and is typically prepared by soaking in a lipid solution a lipid-impregnatable membrane (or a membrane with a quality allowing lipid impregnation) such as a porous membrane. The lipid-impregnated membrane according to this embodiment was prepared by immersing a cellulose ester membrane filter (nominal pore size: 0.1 µm) in an n-decane solution containing soybean lecithin (200 mg/ml) for 10 min. Advantageously, such lipid-impregnated membrane is easy to prepare and has a great strength. Besides the above-described cellulose ester membrane filter, the material of the porous membrane can be exemplified by cellulose, polytetrafluoro ethylene, or polycarbonate.

[Production of Biological Oscillating Device]

Figure 3A:
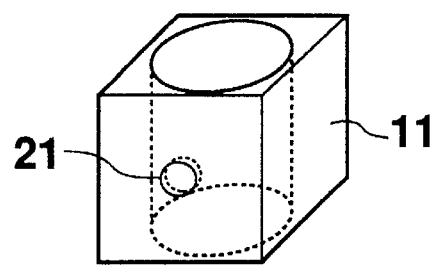
FIGS. 3(A) to 3(C) depict various steps of a method of manufacturing the biological oscillating device according to the embodiment of the present invention using a lipid-impregnated membrane.
Figure 3B:
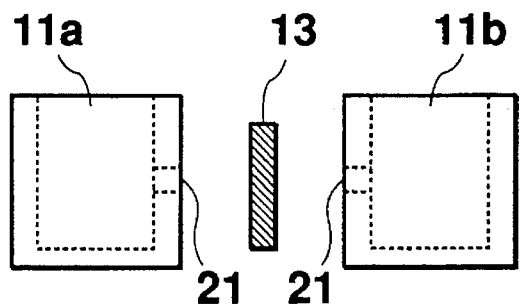
Figure 3C:
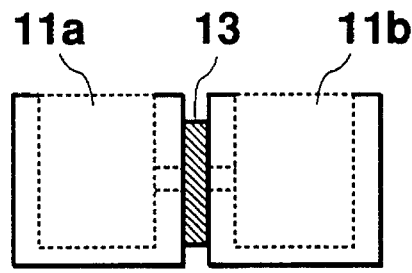

FIG. 3(A) to 3(c) depict various steps for producing a biological oscillating device of this embodiment.

The biological oscillating device of this embodiment is produced by preparing two cells 11a and 11b of fluorocarbon polymer whose mating surfaces have respective holes 21 (FIG. 3(A)) and by sandwiching the lipid-impregnated membrane 13 therebetween (FIG. 3(B)). Thus, the lipid-impregnated membrane 13 formed in accordance with the previously described method is sandwiched between the mating surfaces having the holes 21 to define a structure in which two compartments are partitioned by the lipid-impregnated membrane (FIG. 3(C)). The holes 21 define the hole H in cooperation (FIG. 2). In this embodiment, the holes 21 provided in the mating surfaces have a diameter of 7 to 8 mm, and both the cells 11a and 11b of the fluorocarbon polymer have a volume of 1.5 cc.

Then, the compartments X and Y were both filled with KCl aqueous solution of 0.1 mol/l and allowed to stand for about 1 hour. 100 µl of purple membrane (PM) liposome (400 µg/ml, 0.1 mol/l KCl) was added to the compartment X, whereas 100 µl of 0.1 mol/l KCl aqueous solution was added to the compartment Y. Further, 75 µl (50 mmol/l) of $CaCl_2$ aqueous solution (1 mol/l) was added to both the compartments and stirred for about 1 h. As a result, an ion pump (PM liposome) was buried in the lipid-impregnated membrane 13 on the side of the compartment X. More specifically, a liposome obtained by reconstituting the purple membrane (PM) which consists of bacteriorhodopsin (bR) acting as an ion pump was buried in the lipid-impregnated membrane.

Afterwards, the solution within the compartment Y was substituted with 1.6 ml of KCl aqueous solution (0.5 mol/l), and then 300 µl (1 mol/l KCl) was added thereto to obtain a final salt concentration of 0.58 mol/l KCl in the compartment Y. To the compartment X, on the other hand, 300 µl of KCl aqueous solution of 1 mol/l was added to obtain a final salt concentration of 0.24 mol/l KCl in the compartment X, which was left untouched for about 12 h.

After this 12-hour leaving, 5 µl of ethanol solution containing alamethicin (100 µg/ml) and 5 µl of protamine solution (10 mg/ml) were added to the compartment Y and stirred for about 30 sec. As a result of this, protamine was adsorbed to the lipid-impregnated membrane 13 on the side of the compartment Y, and an ion channel (alamethicin) was reconstituted. With the adsorption of protamine, the surface of the lipid-impregnated membrane 13 on the side of the compartment Y is positively charged in the presence of a neutral solution so that the compartment Y-side lipid-impregnated membrane 13 will possess anion selectivity. That is, although the lipid-impregnated membrane 13 itself inherently presents cation selectivity, the addition of protamine will allow the lipid-impregnated membrane 13 to be partially or wholly converted into anion selective.

It will be appreciated that the protein to be added is not limited to the protamine and that other basic proteins such as spermin are available for the conversion from cation into anion selectivity. The concept "anion selectivity" used herein is a concept that is determined by the relationship with the ion selectivity of the ion channel, and in no way refers to only the state in which the lipid-impregnated membrane 13 is overall positively charged. For example, this concept will cover a case where the membrane is considered to substantially present an anion selectivity, though the sum total becomes negative, since a main part thereof is positively charged.

Thus, by virtue of the conversion of the lipid-impregnated membrane 13 into anion selective, in this embodiment, an ion channel allowing only cation to pass therethrough when reaching a predetermined electric potential can be buried in the anion selective membrane allowing passage of only anions. This combination will ensure an oscillating phenomenon described hereinbelow.

[Action of Biological Oscillating Device]

As described before (See FIG. 2), the compartment X side was connected to ground in the biological oscillating device of this embodiment. Under this state, the compartment Y side was subjected to a constant-current stimulus to observe variations in the membrane potential. That is, in this embodiment, the electrodes 16 are used to effect the constant-current stimulus to cause a membrane potential within the lipid-impregnated membrane 13. The constant-current stimulus was gradually strengthened in a stepwise manner, such as, for example, 0.02, 0.04, 0.08, 0.11, and 0.18 nA.

Figure 4:
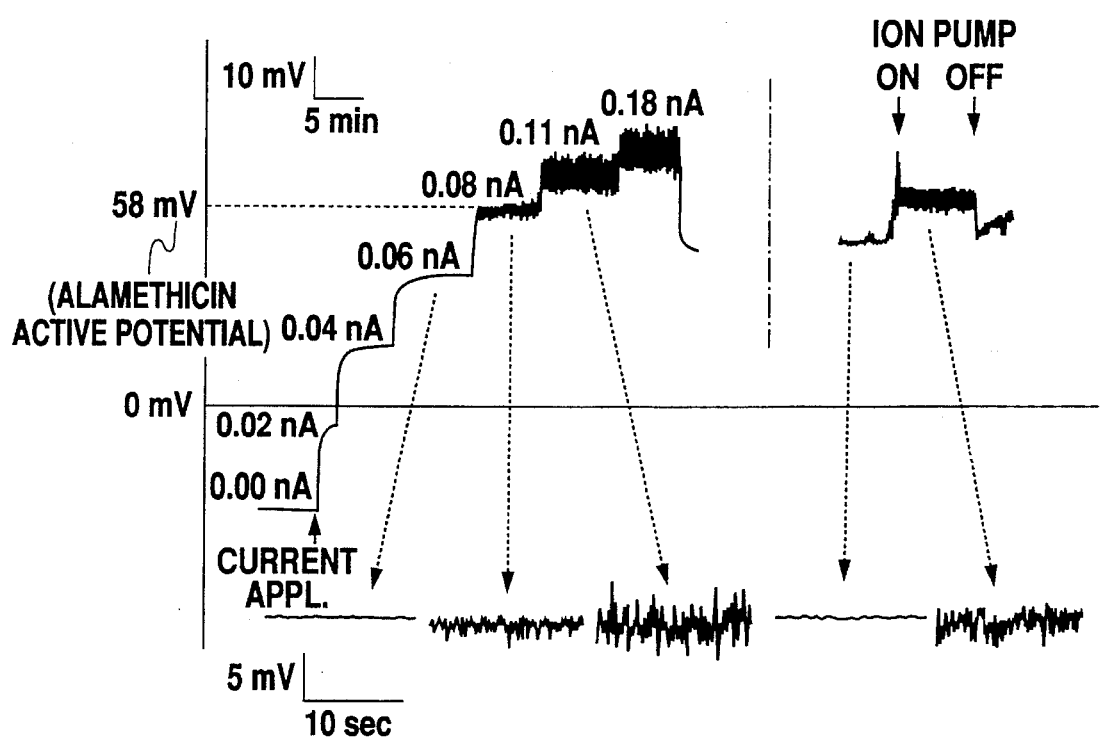
FIG. 4 shows an oscillating electrical signal to be obtained by the biological oscillating device according to the embodiment of the present invention.

The variations in the membrane potential of the lipid-impregnated membrane 13 can be detected by the electrodes 16. The results are shown in FIG. 4 where numerals in the graph signify the magnitude of the constant-current stimulus and the axis of ordinates represents the magnitude of the membrane potential. In this embodiment, an oscillating signal was observed with a constant-current stimulus in the vicinity of 0.08 nA. The reason the oscillating signal is generated by the constant-current stimulus around 0.08 nA is assumed to be that the constant-current stimulus having such a degree of magnitude will cause a membrane potential of the order of 60 mV, which corresponds to the active potential of the alamethicin (ion channel), across the lipid-impregnated membrane 13.

That is, a membrane potential is caused across the lipid-impregnated membrane 13 by the application of a constant-current stimulus. With the increment of the stimulus, the membrane potential increases and the ion channel opens when the membrane potential reaches the active potential of the ion channel, so that the selectivity of the lipid-impregnated membrane 13 is substantially governed by the selectivity of the ion channel. In this embodiment, the lipid-impregnated membrane 13 presents anion selectivity with the addition of protamine but, when the cation selective ion channel opens, will exhibit cation selectivity as a whole. This will result in a drop in the membrane resistance accordingly, and hence in a drop in the membrane potential. Upon the drop of the membrane potential, the ion channel is closed. The membrane potential is again raised by the successive constant-current stimulus to reopen the ion channel, again resulting in a drop in the membrane potential. From the repetition of such procedures, a predetermined fluctuating phenomenon in the membrane potential is obtained, via the electrodes 16.

A disturbance may appear in the waveform of the oscillating signal when the magnitude of the constant-current stimulus exceeds 0.08 nA toward 0.11 and 0.18 nA. It is believed that this arises from the fact that, with increasing constant-current stimulus, interaction among alamethicin channels is increased and hence their opening or closing actions become complicated.

[Concentration of Solution]

In this embodiment, the compartment Y had a final salt concentration of 0.58 mol/l KCl, while the compartment X had a final salt concentration of 0.24 mol/l KCl. Under this condition, the oscillating signals were obtained. Inversely, if the salt concentration within the compartment X is 0.52 mol/l and the salt concentration within the compartment Y is 0.24 mol/l, then no oscillating signals will occur. Also, if both the compartments have the same concentration, no oscillating signals will occur. From such facts, it may be assumed to some extent that the salt concentration within the compartment Y to which side the alamethicin (ion channel) is added must be greater than that within the compartment X.

On the contrary, however, when the ratio of concentration within the two compartments (compartment Y/compartment X) is extremely large, for example, when the ratio is 10, it is not possible to observe any oscillating signals. This will lead to an assumption that there may exist a predetermined appropriate value in the ratio of concentration within the two compartments allowing the oscillating signals to occur. Assumedly, the appropriate value of the ratio of concentration within the two compartments will be determined by the type and state of the lipid-impregnated membrane 13, the temperature of the electrolyte solution 12, the type of the ion channel, and so on. In the case of this embodiment, compartment X/compartment Y=0.58/0.24 seems to have been appropriate.

[Operation of Ion Pump]

For the biological oscillating device of this embodiment, as described before, not only the ion channel but also the ion pump (PM liposome) is buried in the lipid-impregnated membrane 13. This ion pump is activated in response to light irradiation from the light source 14. It is preferable in this case that the light source 14 be disposed on the side at which the ion pump is buried as shown in FIG. 2 (on the side of the compartment X in FIG. 2) since the efficiency is reduced by the amount of light absorbed by the membrane, although a similar oscillation is obtained with the light source 14 oppositely arranged due to a degree of transparency of the lipid-impregnated membrane.

When the ion pump (PM liposome) is activated by the light irradiation, oscillating signals are generated as shown in the right part of FIG. 4. The reason for this is that the proton is transported by the action of the ion pump to thereby cause a membrane potential.

More specifically, when the lipid-impregnated membrane 13 is irradiated by the light source 14, the buried ion pump (PM liposome) is activated to transport protons to cause a membrane potential across the lipid-impregnated membrane 13. Once the thus caused membrane potential reaches a predetermined value, the ion channel opens to reverse the selectivity of the membrane and the membrane resistance is reduced. Then, the ion channel is closed, and the membrane potential is again raised by the action of the ion pump. It is therefore possible through the repetition of such procedures to obtain a predetermined fluctuating phenomenon, with the result that this variation is grasped by the electrode 16 and is output in the form of an oscillating electrical signal.

Thus, according to the biological oscillating device of this embodiment, oscillations as shown in FIG. 4 are obtained when the membrane potential is increased so as to reach the active potential of the ion channel. It will be appreciated that the thus obtained oscillating electrical signal representing a fluctuating phenomenon in the membrane potential is significantly similar to the oscillating phenomenon in the membrane within the living organism.

Also, it is possible for the biological oscillating device of this embodiment to control the ion transporting ability of the ion pump in response to an external stimulus (such as light irradiation), whereby an oscillating electrical signal having an optional oscillating mode corresponding to the external stimulus can be obtained. Accordingly, the biological oscillating device of this embodiment is capable of easily obtaining and readily controlling such an oscillating phenomenon.

Although alamethicin and purple membrane are respectively used as an ion channel and ion pump, other materials are also available. To obtain a predetermined oscillating electrical signal, the lipid-impregnated membrane may comprise other substances without being limited to the materials used in this embodiment.

In this embodiment, the oscillating signals are derived from a combination of an anion selective membrane and a cation selective ion channel. Conversely, a combination of a cation selective membrane and an anion selective ion channel may be employed to obtain oscillating signals based on a similar principle. It is however to be noted in this case that the salt concentration must be set in a manner inverse to this embodiment.

According to the present invention, as described above, when an ion channel having a selectivity opposite to that of a partition membrane is buried into the membrane and the salt concentration, is preferably settled, it is possible to obtain an oscillating phenomenon of the membrane potential and an oscillating electrical signal having an optional oscillating mode corresponding to an external stimulus. This signal is an oscillation element to the nucleus of a bio-information processing system and hence can be the base of a biocomputer.

What is claimed is:

1. A biological oscillating device for generating an oscillating electrical signal, comprising:

(a) a container having two compartments and a passage extending between said two compartments;

(b) two electrolyte solutions each stored in a respective one of said compartments, each solution having a concentration and the concentration of one solution being different from the concentration of the other solution;

(c) a partition membrane extending across said passage for partitioning said compartments from one another, said partition membrane including an ion channel buried thereinto, said ion channel having a cation selectivity and capable of opening when a potential difference between opposite sides of said partition membrane reaches a predetermined threshold value, said partition membrane having an anion selectivity;

(d) means for causing a membrane potential across said partition membrane; and (e) an electrode for transmitting in the form of an electrical signal a variation in the membrane potential caused across said partition membrane; wherein (f) the difference in concentration between said solutions is set in accordance with the selectivity of said partition membrane and of said ion channel.

2. A biological oscillating device according to claim 1, wherein said means for causing a membrane potential across said partition membrane includes:

an ion pump buried in said partition membrane; and means for conferring a stimulus onto said ion pump to actvate said ion pump.

3. A biological oscillating device according to claim 2, wherein said ion channel is alamethicin, and wherein said ion pump is a bacteriorhodopsin (bR).

4. A biological oscillating device according to claim 1, wherein said ion channel is alamethicin.

* * * * *